(12) United States Patent
Tse

(10) Patent No.: US 8,097,033 B2
(45) Date of Patent: Jan. 17, 2012

(54) EXTRAOCULAR MUSCLE PROSTHESIS

(75) Inventor: David T. Tse, Miami, FL (US)

(73) Assignee: The University of Miami, Miami, FL (US)

( * ) Notice: Subject to any disclaimer, the term of this patent is extended or adjusted under 35 U.S.C. 154(b) by 1117 days.

(21) Appl. No.: 11/451,420

(22) Filed: Jun. 13, 2006

(65) Prior Publication Data

US 2006/0287720 A1 Dec. 21, 2006

Related U.S. Application Data

(60) Provisional application No. 60/690,897, filed on Jun. 16, 2005.

(51) Int. Cl.
*A61F 2/16* (2006.01)
*A61F 2/08* (2006.01)

(52) U.S. Cl. ...................... 623/6.64; 623/4.1; 623/13.13; 623/13.14

(58) Field of Classification Search ................. 623/6.64, 623/4.1, 13.13, 13.15, 13.16, 13.14
See application file for complete search history.

(56) References Cited

U.S. PATENT DOCUMENTS

| 3,940,803 | A |   | 3/1976 | Weis, Jr. et al. |        |
|-----------|---|---|--------|------------------|--------|
| 4,087,867 | A | * | 5/1978 | Hickmann et al.  | 623/6.64 |
| 4,955,910 | A |   | 9/1990 | Bolesky          |        |
| 5,292,249 | A | * | 3/1994 | German           | 433/22 |
| 5,487,741 | A | * | 1/1996 | Maruyama et al.  | 606/60 |
| 5,496,355 | A |   | 3/1996 | Lipsky           |        |
| 5,522,889 | A |   | 6/1996 | Baker et al.     |        |
| 5,797,932 | A |   | 8/1998 | Min et al.       |        |
| 5,900,246 | A | * | 5/1999 | Lambert          | 424/429 |
| 6,224,630 | B1 | * | 5/2001 | Bao et al.      | 623/17.16 |
| 6,309,418 | B1 |   | 10/2001 | Jobe            |        |
| 7,329,121 | B2 | * | 2/2008 | De Clerck       | 433/18 |
| 2003/0176920 | A1 | * | 9/2003 | Sklar et al.  | 623/13.13 |
| 2004/0073303 | A1 | * | 4/2004 | Schanzlin et al. | 623/5.16 |
| 2004/0236327 | A1 | * | 11/2004 | Paul et al.   | 606/61 |
| 2005/0125059 | A1 | * | 6/2005 | Pinchuk et al. | 623/6.56 |
| 2005/0125060 | A1 | * | 6/2005 | Perry et al.  | 623/6.64 |
| 2006/0190039 | A1 | * | 8/2006 | Birk et al.   | 606/219 |
| 2007/0088432 | A1 | * | 4/2007 | Solovay et al. | 623/4.1 |

FOREIGN PATENT DOCUMENTS

WO    WO 02/091941 A1 * 11/2002

OTHER PUBLICATIONS

PCT International Search Report dated Apr. 16, 2007 issued in copending PCT Application PCT/US 06/23016.
Morad et al; "Lateral Rectus Muscle Disinsertion and Reattachment to the Lateral Orbital Wall"; Scientific Report; Br. J. Ophthalmol. 2005; 89 pp. 983-985.

(Continued)

*Primary Examiner* — Paul Prebilic
(74) *Attorney, Agent, or Firm* — Nixon & Vanderhye PC

(57) ABSTRACT

A prosthetic device and method to restore extraocular muscle function. The device includes a housing; a biasing component disposed in the housing; a proximal connector operatively connected to a proximal end of the biasing component; and a distal connector operatively connected to a distal end of the biasing component, wherein the proximal connector is configured for being secured with respect to an orbital bone and the distal connector adapted to be secured to the paralyzed or absent muscle stump, e.g. on the globe, or to the eyelid.

12 Claims, 3 Drawing Sheets

OTHER PUBLICATIONS

Bicas, Harley; "A Surgically Implanted Elastic Band to Restore Paralyzed Ocular Rotations"; Journal of Pediatric Ophthalmology & Strabismus; Jan./Feb. 1991, vol. 28, No. 1; pp. 10-13.

Scott et al; "Eye Muscle Prosthesis"; Journal of Pediatric Ophthalmology & Strabismus; Jul./Aug. 1992, vol. 29, No. 4; pp. 216-218.

Goldberg et al; "Use of Apically Based Peristeal Flaps as Globe Tethers in Severe Paretic Strabismus"; Arch Ophthalmology; Mar. 2000, vol. 118; pp. 431-437.

Aguirre et al; "Static and Dynamic Mechanical Testing of a Polymer with Potential Use as Heart Valve Material"; 2003 Summer Bioengineering Conference; Jun. 25-29, Sonesta Beach Resort in Key Bascayne, Florida; pp. 1039-1040.

* cited by examiner

EXTRAOCULAR MUSCLE PROSTHESIS

CROSS-REFERENCE TO RELATED APPLICATION

This application claims the benefit of Provisional Application No. 60/690,897, filed Jun. 16, 2005, the entire content of which is hereby incorporated by reference in this application.

BACKGROUND OF THE INVENTION

Classic examples of paralyzed extraocular muscle are congenital or acquired complete third nerve palsy and ocular fibrosis syndrome. An ophthalmic complication encountered with increasing frequency in functional endoscopic sinus surgery (FESS) is inadvertent amputation of the medial rectus muscle. The consequence of such medial rectus dysfunction is that the involved eye assumes a large angle exotropia, an inability to adduct the eye, and disabling diplopia. Occasionally, severe paralytic and restrictive or absent extraocular muscle will require globe fixation in the primary position because of the presence of an active antagonist muscle.

Surgical remedies include supramaximal recession of the lateral rectus and transposition of the vertical muscles to replace the lost motor function of the transected medial rectus, or passively fixating the globe to the periosteum of the medial wall. Unfortunately, operating on the remaining three rectus muscles could compromise the blood supply to the eye, leading to anterior segment ischemia and reduced visual acuity. Attaching the eye to the medial wall periosteum fixates the globe into one primary position permanently, rendering it unable to abduct and thus negating the effect of the normal functioning lateral rectus muscle. Permanent suture material and autogenous fascia such as temporalis fascia attached to the remnant of the transected muscle have been attempted. Use of the apically based periosteal flap to tether the globe in primary position has been advocated. (Goldberg R A, Rosenbaum A L, Tong J T; "Use of apically based periosteal flaps as globe tethers in severe paretic strabismus"; *Arch Opthalmol* 2000; 118; 431-437). All these surgical options share one major drawback—the globe is tethered to one position, unable to adduct or abduct the eye. Scott and Associates (Scott A B, Miller J M, Collins C C; "Eye Muscle Prosthesis"; *J Pediatr Opthalmol Strabismus,* 1992; 29:216-218) inserted a silicone rubber band along the course of the paralyzed muscle to restore alignment and to provide an elastic band against which the antagonist could pull. In their cases, there was a reduction in motility in the first or second month following surgery. The authors attributed the reduced motility to the development of a fibrous membrane surrounding the implant which acts as a further restriction to the antagonist. Bicas (Bicas HEA, "A surgically implanted elastic band to restore paralyzed ocular rotations"; *J Pediatr Ophthalmol Strabismus.* 1991; 28:10-13) placed a doubled 1-millimeter silicone tubing from the front of the globe to the orbit. This is an improvement over purely holding the eye to the orbital periosteum with sutures, as the implanted elastic band provides a posteriorly directed vector.

BRIEF SUMMARY OF THE INVENTION

It is an object of the invention to provide an eye (globe) muscle prosthesis that overcomes the drawbacks of the currently available treatment options described above. It is another object of the invention to provide an eyelid muscle prosthesis for treatment of ptosis with poor levator function.

These and other objects are realized by providing an eye muscle prosthetic spring to replace a paralyzed or absent extraocular muscle. In an example embodiment, a biasing component is housed in an elastic or stretchable polymeric material so as to avoid an inflammatory reaction. The spring prosthesis, housed in this protective envelope, provides tension in the primary position to balance the antagonistic natural eye muscle while resisting linear elasticity to permit eye movement initiated by the antagonist muscle.

Thus, the invention may be embodied in a prosthetic device for implantation to restore extraocular muscle function comprising: a housing; a biasing component disposed in said housing; a proximal connector operatively connected to a proximal end of the biasing component; and a distal connector operatively connected to a distal end of the biasing component, wherein said proximal connector is configured for being secured with respect to an orbital bone and said distal connector adapted to be secured to the globe of the eye. In an example embodiment, a T-plate fixation provides a firm anchor for the prosthesis in a posteriorly directed vector.

The invention may also be embodied in a method for restoring muscle function comprising: providing a muscle prosthesis including a housing and a biasing component disposed in said housing, connecting a distal end of at least one of the housing and the biasing component to the globe of the eye; and connecting a proximal end of at least one of the housing and the biasing component to the orbital bone.

The invention may also be embodied in a prosthetic device for restoring eyelid function comprising: a housing; a coil spring component disposed in said housing; a proximal connector operatively connected to a proximal end of the biasing component; and a distal connector operatively connected to a distal end of the biasing component, wherein said proximal connector is configured for being secured with respect to an orbital bone and said distal connector adapted to be secured to the upper eyelid.

BRIEF DESCRIPTION OF THE DRAWINGS

These and other objects and advantages of this invention, will be more completely understood and appreciated by careful study of the following more detailed description of the presently preferred exemplary embodiments of the invention taken in conjunction with the accompanying drawings, in which.

DETAILED DESCRIPTION OF THE INVENTION

Figure 1:
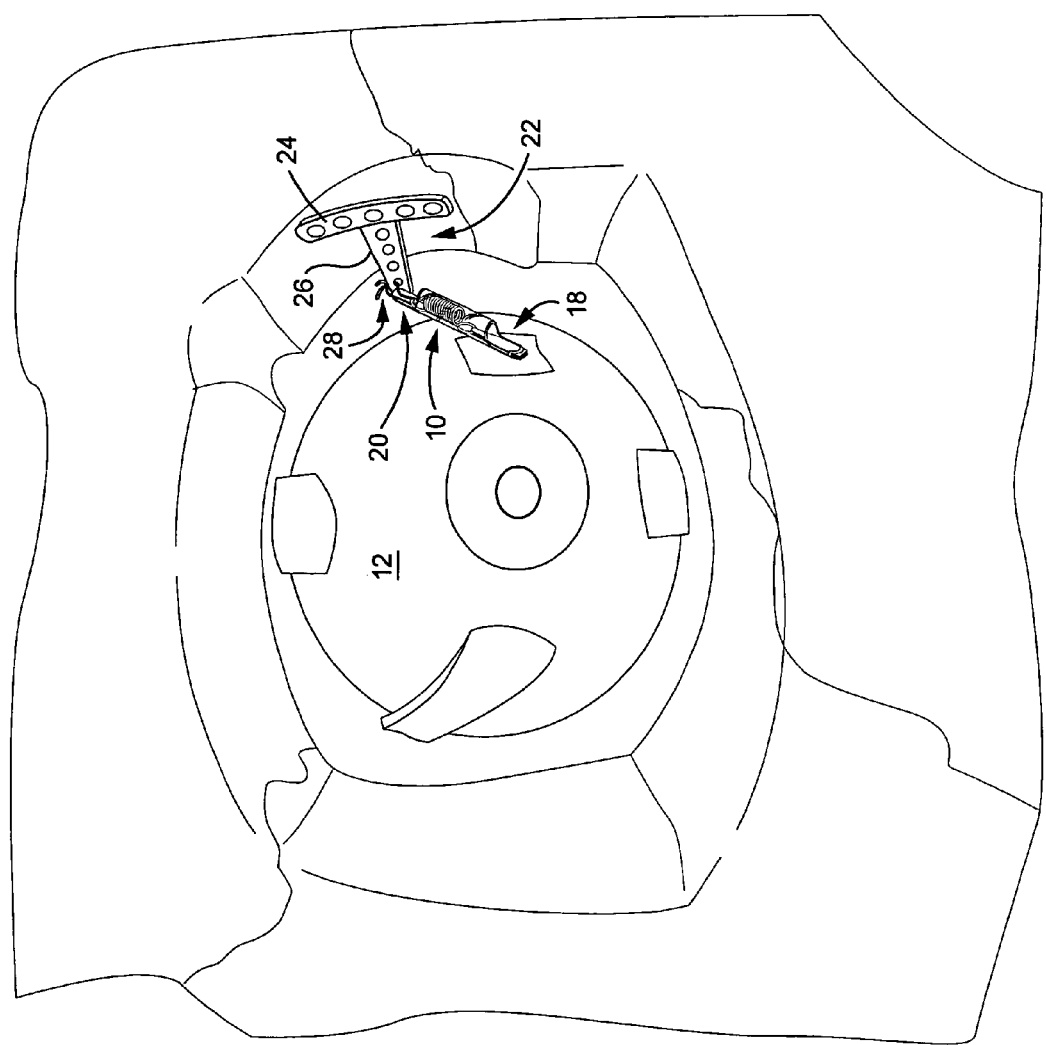
FIG. 1 schematically illustrates an eye muscle prosthesis embodying the invention extending between the medial rectus stump and the distal end of a titanium T-plate anchored to the nasal bone so that the eye muscle prosthesis provides a posteriorly directed vector.

An eye muscle prosthesis is provided in an example embodiment of the invention to replace a paralyzed or absent extraocular muscle. More specifically, an eye muscle prosthesis is provided comprising a spring device 10 for biasing the globe 12 of the eye to the primary position. The spring device includes an outer housing 14, a component 16 for biasing the globe to the primary position, a connector 18 for operatively connecting one end of the biasing component to the globe, and a connector 20 for operatively connecting the other end of the biasing component to the boney perimeter of the orbit.

In the illustrated example embodiment, the biasing component is a coil torsion spring. In an example embodiment of the invention, the spring is formed from ELGILOY® (Co-20Cr-16Fe-15Ni-7Mo), although other materials such as titanium, Nitinol, stainless steel or the like, which are known for their biocompatibility and resistance to corrosion as well as suitability for minute spring components, could be used. In this regard, ELGILOY® is highly corrosion resistant with high fatigue strength and is known and used for human implants. Titanium is also strong, lightweight and highly resistant to corrosion. Its strength is comparable to 304 stainless steel and it is known and used for human implants. Nitinol is a shape memory alloy. Its unique characteristics allow it to return to a predetermined shape after undergoing deformation. Nitinol has excellent biocompatibility, good spring characteristics and high corrosion resistance. For ease of description, the biasing component will hereinafter generically be referred to as the spring. It is to be understood, however, that biasing components other than coil torsion springs may be used in the practice of the invention.

The housing 14 defines an internal cavity having a chamber for receiving the spring 16 and is made of a polymeric material selected so as not to elicit any inflammatory rejection nor create a fibrotic surrounding that would impair the spring function. As presently proposed, the polymer defining the envelope or housing 14 receiving and protecting the spring is polystyrene-polyisobutylene-polystyrene or poly(styrene-b-isobutylene-b-styrene) (SIBS). This is a material developed for implant applications and has been found to be less likely to degrade in vivo than polyurethane.

In an example embodiment, the housing 14 is a longitudinally flexible sleeve that has resiliency built into the tubing so that it can extend and retract with the spring. In the alternative, the housing can be configured as an accordion structure to extend and retract with the spring. As yet a further alternative, the housing is of generally fixed length, so that the coil spring expands and contracts within the housing and one or the other connector selectively pays-out from the housing as the spring extends and retracts into the housing as the spring retracts. In any case, a seal is defined at each longitudinal end of the housing 14 to seal the spring 16 and the joints to the connectors from the biological fluids completely, as described more particularly below. In this respect, the construction of the muscle prosthesis is analogous to a shock absorber in which the spring is housed within a casing, protected from the external environment.

In an example embodiment, as schematically illustrated in FIG. 1, the distal connector 18 comprises a tab component extending from the spring 16 to connect the spring to the globe 12. The distal end of the tab may be secured by non-absorbable suture or other means to, e.g., the insertion of the involved muscle on the globe. In an example embodiment the tab is a SIBS-coated Dacron mesh that is secured to the medial rectus stump with non-absorbable sutures.

The proximal end of the prosthesis in the illustrated example embodiment is secured to the nasal bone. In the presently proposed embodiment, the prosthesis is not attached directly to the bone but rather is attached to the bone through a bone plate. In the illustrated example, the bone plate is a T-shaped plate 22 formed from titanium. The T-shape of the bone plate allows the bone plate to be selectively secured at spaced locations along the horizontal bar 24 by screws, thereby distributing stress along a corresponding length of the bone. The vertical bar 26 of the T-plate 22 projects towards the orbital apex along the medial wall. The proximal end of the prosthesis is attached to the vertical bar with a non-absorbable suture 28 by tying. Although in the illustrated embodiment, the bone plate is illustrated as secured to the nasal bone, it is to be understood that the bone plate would be attached, e.g., to the lateral orbital wall where the muscle prosthesis is used to correct a paralytic lateral rectus muscle, to the inferior orbital rim to correct inferior rectus muscle paralysis, or to the superior orbital rim for correction of superior rectus/levator muscle paralysis.

Figure 2:
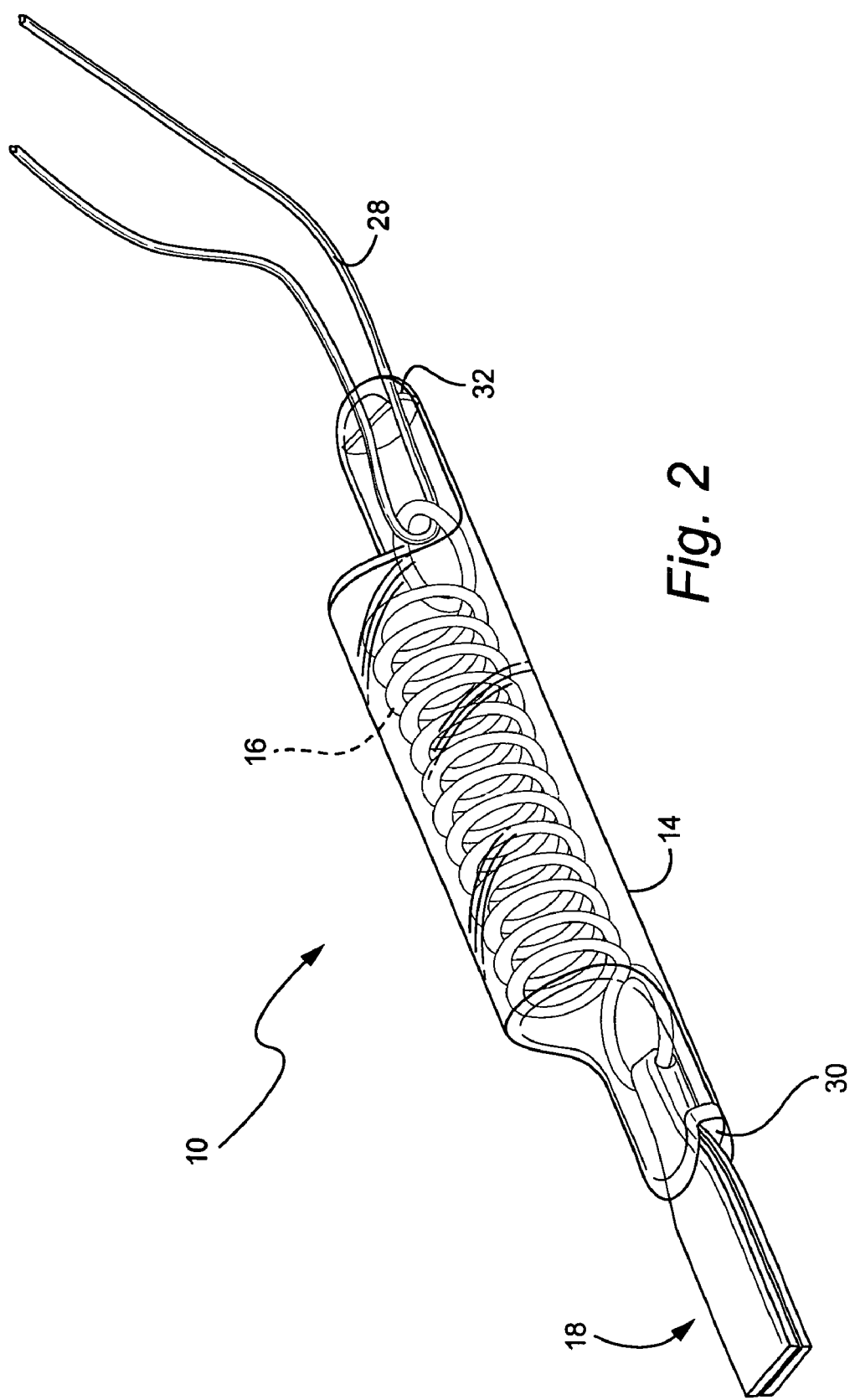
FIG. 2 is an enlarged schematic perspective view of a extraocular muscle prosthesis embodying the invention.

As mentioned above, a seal is defined at each longitudinal end of the housing 14, to seal the spring 16 from the biological fluids completely. In the case where the housing extends and contracts with the spring, the housing may be solvent bonded closed at each end with the respective connector structures extending through the respective end seals. Thus, as illustrated in FIG. 2, the tab component extends through a seal 30 at the distal end of the housing so that it is attached to the spring and fixed with respect to the housing. Similarly, the suture connector 28 extends through a seal 32 at the proximal end of the housing so that it is attached to the spring and fixed with respect to the housing. Since the body of the housing is resilient, or is accordion shaped (not shown), and can extend and retract between the sealed ends, the extension/retraction of the prosthesis is realized while the spring remains sealed and isolated from the environment.

On the other hand, in the case where the housing is of fixed length and a part of the biasing component and/or a part of a connector structure must pay-out and retract through one end of the housing, a suitable seal structure can be provided at each longitudinal end to ensure a fluid tight seal at the connector junctions. For example, a bellows seal formed from a flexible biologically inert material (not shown) may be provided to extend between the housing and the extending component so that the component(s) disposed in the housing are isolated and protected from biological fluids which might otherwise inhibit their long term operation and so that the coil spring will not be enveloped by a fibrous membrane that could potentially impair its spring action.

As will be appreciated, to provide proper function, the spring force provided by the coil spring may be selected and the tab length and placement may be determined to meet the needs of each individual patient. As presently proposed the spring force of this embodiment is approximately 0.5-20 grams in tension. In an example embodiment, calibration marks (not shown) on the distal end of the prosthesis indicates the amount of stretch needed to achieve, e.g., a 5 gram or 10 gram tension in the primary position. The spring material and coil configuration is adapted for 10 grams of tension for a defined distance of stretch. To allow eye rotation away from the prosthesis into the field of the antagonist, the stiffness of the prosthetic spring is adjusted to about 0.3 or 0.5 gram per degree for a horizontal muscle. The foregoing stiffnesses and tensions are offered by way of example only and it is to be appreciated that the calibration of the spring, spring tensions, stiffness and the like may be determined and adapted to the particular environment and conditions in which the implant is provided and may be refined through routine experimentation.

As mentioned above, the coil spring prosthesis provides tension in the primary position to balance the antagonist eye muscle while possessing linear elasticity to permit eye movement initiated by the antagonist muscle over as wide a range as possible. The inherent stiffness of the spring however restores the eye to the primary position upon relaxation of the antagonist muscle. Thus, when the antagonist muscle contracts to rotate the eye away from the prosthesis into the field of the antagonist, the SIBS tube, which is flexible and may have an accordion wall, will stretch with the spring. Conversely, when the antagonist muscle relaxes, the coil spring returns toward its non-tensioned position and the SIBS tube relaxes as well.

According to a further feature of the invention, the polymer casing can also be used to carry a medicinal agent or drug to the implantation site and may be adapted for release thereof over time. For example, steroids, anti-fibrotic agents, and/or antimicrobials may be incorporated in the polymeric casing to elute out over time. Once the prosthesis has been placed, the polymer will help control drug release around the site of the implant/prosthetic placement. This will contribute to even and consistent distribution of the drug over time to promote healing, reduce inflammation and enhance the outcome of the procedure.

Although the invention has been described above with reference to a muscle prosthesis for controlling the position of the globe of the eye, it is to be understood that the muscle prosthesis of the invention may be also adapted to replacing or supplementing other muscles in the region of the eye. Thus, by way of example the invention may also be adapted to treat ptosis. Ptosis, the drooping of the upper eyelid, is a condition that may be congenital or acquired. In congenital ptosis, the levator palpebrae superioris muscle that elevates the lid is either absent or imperfectly developed. Acquired or paralytic ptosis is usually due to injury or disease of the nerve that controls the movements of the levator muscle. Thus, it is further object of the invention to provide a method and apparatus of restoring eyelid function in a patient suffering from ptosis.

Figure 3:
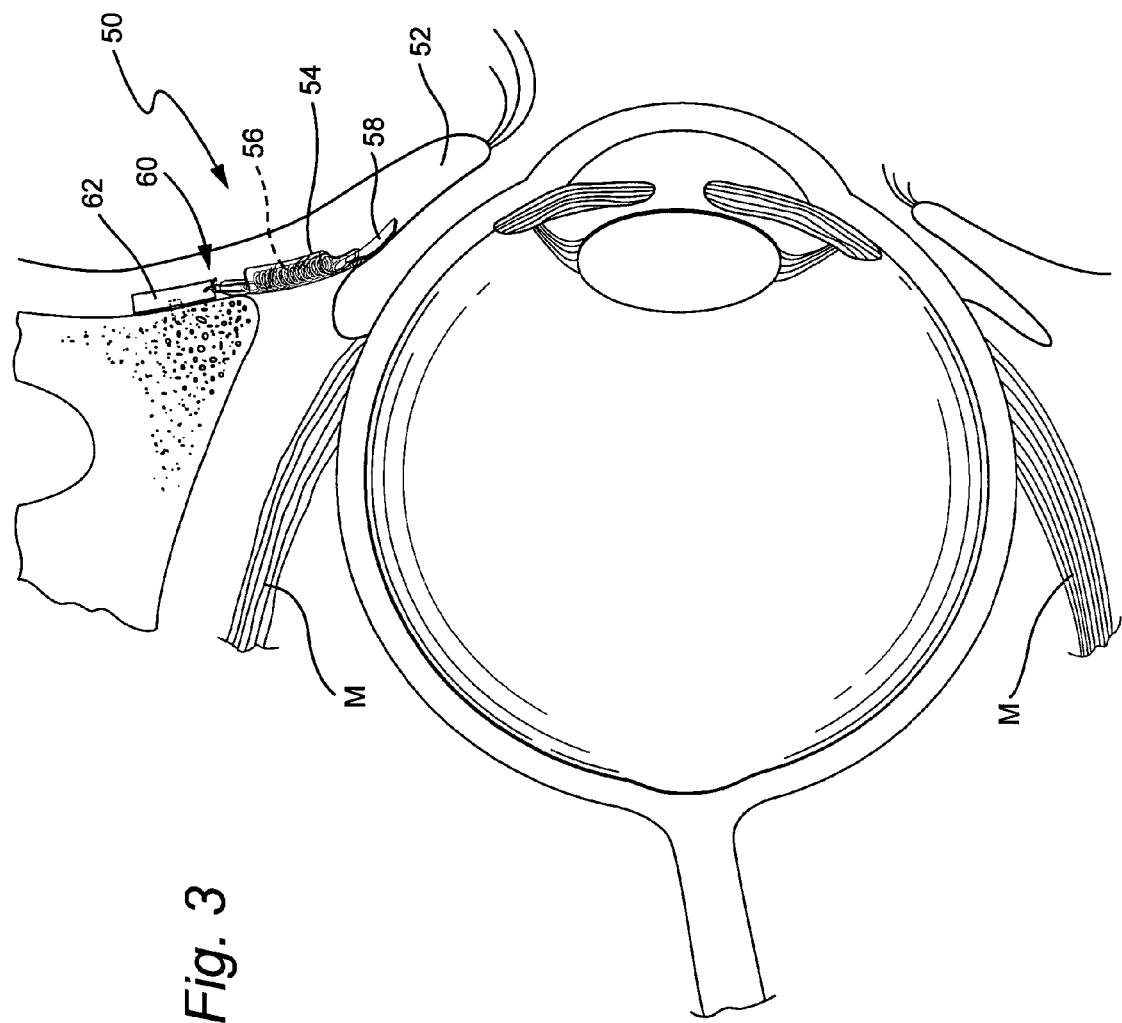
FIG. 3 is a schematic cross-sectional view depicting a muscle prosthesis embodying the invention implanted for treatment of ptosis.

Referring to FIG. 3, in accordance with an alternate example embodiment of the present invention, a method and prosthesis are provided for restoring eyelid function in a patient having a limited ability to voluntarily raise the eyelid. The prosthesis comprises a spring device 50 for biasing the eyelid 52 to an open position. The spring device includes an outer housing 54 formed from a substantially biologically inert material, such as SIBS polymer, a component 56 for biasing the eyelid to an open position, a connector 58 for operatively connecting the housing and/or biasing component to the eyelid 52, and a connector 60 for operatively connecting the housing and/or biasing component to the bone. As in the FIG. 2 embodiment, the housing 54 defines an internal cavity having a chamber for receiving the biasing component which, in the illustrated example embodiment is a spring, more specifically a coil torsion spring. Thus, it is appreciated that the eyelid is raised by the stiffness of the coil spring returning the coil spring to its unextended position, and the eyelid is lowered by stretching the spring. The stretching of the spring is effected by the squeezing function of orbicularis muscle fibers (the orbicularis muscle is the antagonist of the levator muscle). The tension force is selected so as to be sufficient to fully raise the eyelid but not so great as to prevent extension of the spring and closure of the eyelid when the functional weight of the lid increases as a result of the action of the muscles of eye closure when producing a blink. As presently proposed the spring force of this embodiment is proximally 0.5-20 grams in tension.

When placed for corrected ptosis, the proximal end of the eye muscle prosthesis is anchored to the superior orbital rim under the brow, and the distal end is sutured to the tarsal plate. This method of placement is similar to current frontalis suspension techniques for severe ptosis, such a fascia lata or silicone sling procedure.

Thus, in an example embodiment, a plate 62 is fastened to the bone by one or more screws and the proximal end of the prosthesis is secured, e.g. with a non-absorbable suture, to the bone plate. In the alternative, the proximal end of the spring device (housing and/or spring component) could be secured directly to the superior orbital rim.

Further, in an example embodiment, the distal connector 58 comprises a distal tab that extends from the housing 54 to connect the spring to the eyelid 52. The distal end of the tab may be secured by non-absorbable suture or other means to the eyelid. In one example embodiment, the housing can be configured to elongate and shorten with the spring component, or can be defined as an accordion structure to extend and contract with the coil spring, as described and illustrated above with reference to FIGS. 1 and 2.

Alternatively, the housing is of generally fixed length, so that the coil spring expands and contracts within the housing. Thus, when the eyelid closes, the tab pays-out from the housing and the coil spring is extended within the housing. Conversely, when the eyelid opens, the coil spring returns to its non-tensioned position and the tab is drawn back inwardly of the housing. In accordance with this alternative a seal structure such as a bellows seal formed from a flexible biologically inert material (not shown) is provided to extend from the housing to the extendable tab so that the component(s) disposed in the housing are fully sealed and protected from biological fluids that might otherwise inhibit their long term operation and such that the coil spring will not be enveloped by a fibrous membrane that could potentially impair its spring action.

While the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope of the appended claims.

The invention claimed is:

1. A prosthetic device for implantation to restore extraocular muscle function comprising:
   a housing;
   a biasing component disposed in said housing;
   a proximal connector operatively connected to a proximal end of the biasing component; and
   a distal connector operatively connected to a distal end of the biasing component;
   wherein said proximal connector is configured for being secured with respect to an adjacent bone and said distal connector adapted to be secured to a globe of an eye;
   wherein the proximal connector comprises a metal bone plate;
   wherein the bone plate is T-shaped including a vertical bar for attachment to at least one of the housing and the biasing component and a horizontal bar for being attached by at least one screw to the adjacent bone;
   wherein the housing is formed from a polymeric material; and
   further including means for sealing the housing to isolate said biasing component from biological fluids.

2. A prosthetic device as in claim 1, wherein the biasing component has a spring force of approximately 0.5-20 grams in tension.

3. A prosthetic device as in claim 1, wherein said biasing component comprises a helical coil spring.

4. A prosthetic device as in claim 1, wherein the proximal connector further comprises a suture filament.

5. A prosthetic device as in claim 1, wherein an anti-fibrotic agent is incorporated in said polymeric material to elute out over time.

6. A prosthetic device as in claim 1, wherein the housing is of substantially fixed length.

7. A prosthetic device as in claim 1, wherein the sealing means comprises a bellows seal connected to the housing and enveloping at least a part of the distal connector.

8. A prosthetic device as in claim 1, wherein the bone plate is formed from titanium.

9. A prosthetic device as in claim 1, wherein the housing is formed from polystyrene-polyisobutylene-polystyrene or poly(styrene-b-isobutylene-b-styrene) (SIBS).

10. A muscle prosthesis for restoring muscle function, comprising:
- a housing and a biasing component disposed in said housing,
- a distal end of at least one of the housing and the biasing component being adapted to be connected to a globe of the eye or adapted to be connected to an upper eyelid;
- a proximal end of at least one of the housing and the biasing component being adapted to be connected to an adjacent bone by screwing a metal bone plate to the adjacent bone and connecting said proximal end to said metal bone plate,
- wherein said metal bone plate is T-shaped including a vertical bar and a horizontal bar,
- wherein said horizontal bar is adapted to be screwed to the adjacent bone and the proximal end of at least one of the housing and the biasing component is attached to said vertical bar, and
- wherein said proximal end of at least one of the housing and the biasing component is attached to said vertical bar with a suture filament.

11. A muscle prosthesis as in claim 10, wherein said biasing component comprises a helical coil spring and wherein a distal end of a tab component coupled to a distal end of said helical coil spring is adapted to be sutured to the medial rectus stump.

12. A muscle prosthesis as in claim 10, wherein the housing is formed from a polymeric material and wherein an anti-fibrotic agent is incorporated in said polymeric material to elute out over time.

* * * * *